(12) United States Patent
Nelson et al.

(10) Patent No.: US 10,478,621 B1
(45) Date of Patent: Nov. 19, 2019

(54) RETRACTABLE LEAD SYSTEMS

(71) Applicant: General Electric Company, Schenectady, NY (US)

(72) Inventors: David Allen Nelson, Florence, SC (US); Mark Derakhshan, Florence, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/208,102

(22) Filed: Dec. 3, 2018

(51) Int. Cl.
*A61N 1/05* (2006.01)
*A61N 1/375* (2006.01)

(52) U.S. Cl.
CPC ........... *A61N 1/057* (2013.01); *A61N 1/3752* (2013.01)

(58) Field of Classification Search
CPC .. A61N 1/057; A61N 1/3752; H01R 13/6205; H01R 2201/12; H01R 13/5224; H01R 13/7037
USPC ................ 439/135, 700; 200/16 B, 209, 210
See application file for complete search history.

(56) References Cited

U.S. PATENT DOCUMENTS

| | | | | |
|---|---|---|---|---|
| 6,463,334 B1 * | 10/2002 | Flynn | ...................... | A61N 1/056 607/122 |
| 6,501,990 B1 * | 12/2002 | Sundberg | ............... | A61N 1/056 607/122 |
| 8,682,451 B2 * | 3/2014 | Wengreen | .............. | A61N 1/057 607/126 |
| 9,182,464 B2 | 11/2015 | Mine et al. | | |
| 9,276,349 B2 * | 3/2016 | Yoshida | ............... | H05K 7/1474 |
| 2002/0116035 A1 * | 8/2002 | Klehn | ................... | A61N 1/3752 607/37 |
| 2004/0239462 A1 * | 12/2004 | Nemoto | ................... | H01F 6/065 335/216 |
| 2007/0043414 A1 * | 2/2007 | Fifer | ..................... | A61N 1/0565 607/126 |
| 2008/0004683 A1 * | 1/2008 | Wengreen | .............. | A61N 1/057 607/119 |
| 2008/0154296 A1 * | 6/2008 | Taylor | ..................... | A61B 1/32 606/190 |
| 2008/0183266 A1 * | 7/2008 | D'Aquanni | ............ | A61N 1/057 607/126 |
| 2010/0148894 A1 * | 6/2010 | Ohashi | ................... | H02K 55/02 335/216 |

(Continued)

*Primary Examiner* — Harshad C Patel
(74) *Attorney, Agent, or Firm* — Dean D. Small; The Small Patent Law Group, LLC

(57) ABSTRACT

A retractable lead system is provided that includes a cup, a spherical contact, and a plunger. The cup is disposed proximate a vacuum end of the retractable lead system, and defines a cavity and a contact reception seat. The contact reception seat defines a spherical portion having a contact reception spherical radius. The spherical contact is disposed within the contact reception seat, and defines a contact spherical radius that corresponds to the contact reception spherical radius. The spherical contact is configured to be electrically coupled to an interior lead disposed within a vacuum environment. The plunger includes an ambient contact and a retractable contact disposed on opposite ends of the plunger. The plunger is configured to be actuated between an open position at which the retractable contact is retracted from the spherical contact and a closed position at which the retractable contact is coupled with the spherical contact.

20 Claims, 4 Drawing Sheets

(56) References Cited

U.S. PATENT DOCUMENTS

2010/0274338 A1\* 10/2010 Ollivier ............... A61N 1/0573
607/127

\* cited by examiner

RETRACTABLE LEAD SYSTEMS

BACKGROUND OF THE INVENTION

The subject matter disclosed herein relates generally to apparatus and methods for providing a retractable lead system, for example a retractable lead configured to provide electrical communication to an enclosed vacuum environment.

Retractable leads may be used to bring corresponding contacts into and out of contact. However, if flat, rigid contacts are used, full contact may be dependent on machined geometry limitations (e.g., ability to be close to perfectly parallel). Similarly, use of conical and rigid contacts may result in machined geometry differences that result in line contact. Further, multi-point contacts may require lengths of travel that are impractical.

Additionally, retractable leads may be used in connection with enclosed vacuum applications. However, known sealing approaches may provide less effective sealing than is desired. Further, it may be noted that springs may be used to provide a desired load. However, known spring approaches may have drawbacks, including movement of the springs and/or interference by the springs with other components (e.g., springs becoming engaged or caught up in threads or other components).

BRIEF DESCRIPTION OF THE INVENTION

In one example embodiment, a retractable lead system is provided that includes a cup, a spherical contact, and a plunger. The cup is disposed proximate a vacuum end of the retractable lead system, and defines a cavity and a contact reception seat. The contact reception seat defines a spherical portion having a contact reception spherical radius. The spherical contact is disposed within the contact reception seat, and defines a contact spherical radius that corresponds to the contact reception spherical radius. The spherical contact is configured to be electrically coupled to an interior lead disposed within a vacuum environment. The plunger includes an ambient contact and a retractable contact disposed on opposite ends of the plunger. The ambient contact is disposed proximate an ambient end of the retractable lead system. The plunger is configured to be actuated between an open position at which the retractable contact is retracted from the spherical contact and a closed position at which the retractable contact is coupled with the spherical contact.

In another example embodiment, a retractable lead system is provided that includes a cup, a seated contact, a plunger, and a sealing member. The cup is disposed proximate a vacuum end of the retractable lead system, and defines a cavity and a contact reception seat. The seated contact is disposed within the contact reception seat, and is configured to be electrically coupled to an interior lead disposed within a vacuum environment. The plunger includes an ambient contact and a retractable contact disposed on opposite ends of the plunger. The ambient contact is disposed proximate an ambient end of the retractable lead system. The plunger is configured to be actuated between an open position at which the retractable contact is retracted from the seated contact and a closed position at which the retractable contact is coupled with the seated contact. The sealing member is configured to be disposed a distance from a vacuum end plate disposed proximate a boundary of the vacuum environment and having an opening through which the plunger passes. The plunger moves relative to the vacuum end plate when moved between the open and closed positions.

In another example embodiment, a retractable lead system is provided that includes a cup, a seated contact, a plunger, a drive stud and drive nut, and a resiliently biasable spring assembly. The cup is disposed proximate a vacuum end of the retractable lead system. The cup defines a cavity and a contact reception seat. The seated contact is disposed within the contact reception seat, and is configured to be electrically coupled to an interior lead disposed within a vacuum environment. The plunger includes an ambient contact and a retractable contact disposed on opposite ends of the plunger. The ambient contact is disposed proximate an ambient end of the retractable lead system. The plunger is configured to be actuated between an open position at which the retractable contact is retracted from the seated contact and a closed position at which the retractable contact is coupled with the seated contact. The drive stud coupled to the plunger. The resiliently biasable spring assembly is disposed radially about the drive stud.

DETAILED DESCRIPTION OF THE INVENTION

Figure 1:
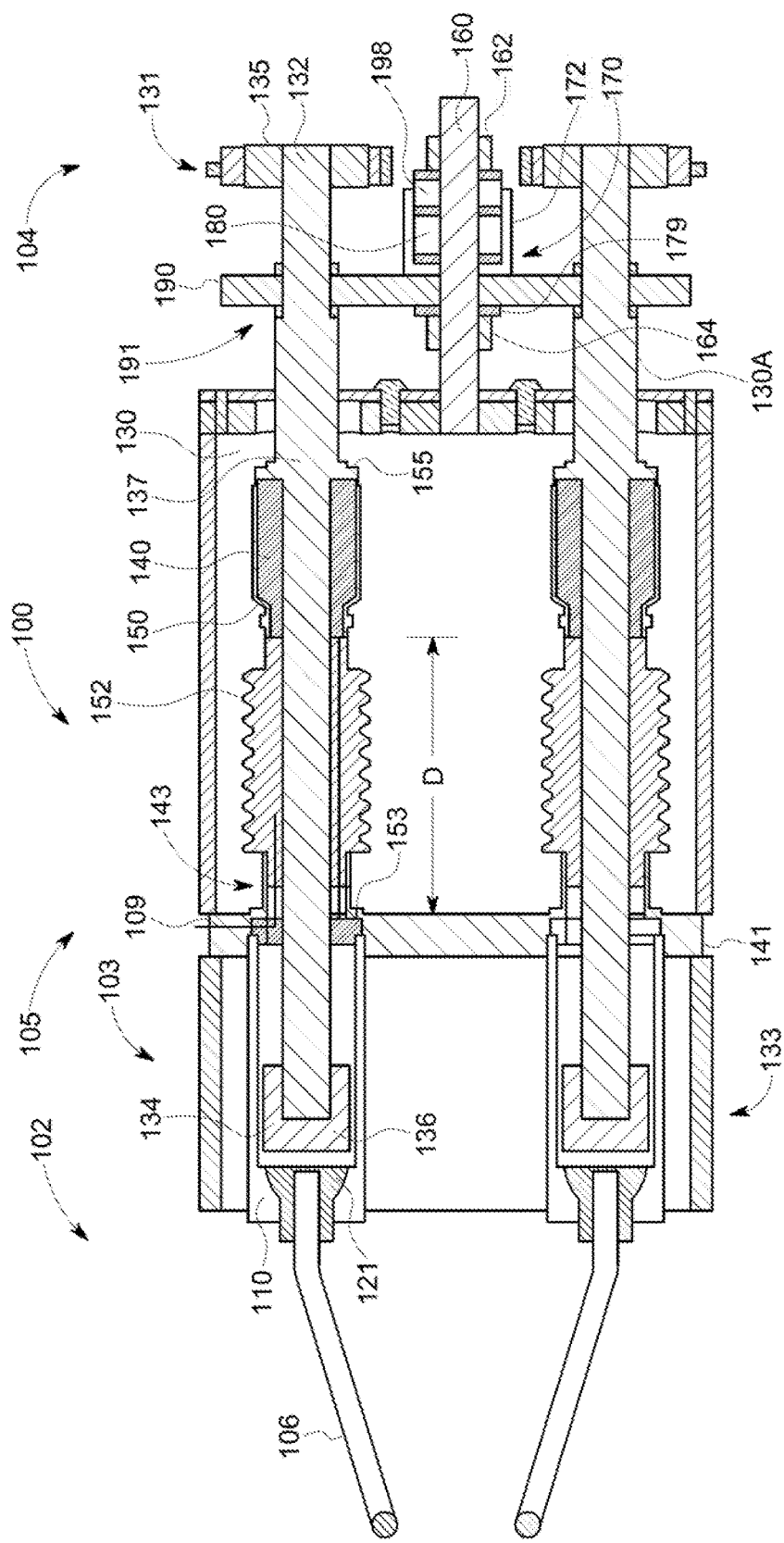
FIG. 1 provides a side sectional view of a retractable lead system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware. It should be understood that the various embodiments are not limited to the arrangements and instrumentality shown in the drawings.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide improved retractable lead performance. For example, various embodiments provide spherical contacts that promote automatic contact alignment and improved or maximized contact area with consistent results. Various embodiments also provide a spring guide (e.g., a spring cup) that provides a housing for spring members (e.g., Belleville washers) that pilot on a drive stud and guides the spring members to prevent the spring members from slipping into threads and inadvertently locking up a drive mechanism. Various embodiments also provide a welded ceramic seal that provides improved sealing relative to epoxy. For example, a welded ceramic seal in various embodiments provides superior sealing reliability in a cryostat environment, and provides torsional failure resistance that may be an order of magnitude greater than that provided by an epoxy based design.

A technical advantage of various embodiments includes improved retractable leads for use with vacuum environments. A technical advantage of various embodiments includes improved positioning of springs that provide a load to a retractable lead system. A technical advantage of various embodiments includes improved sealing of retractable lead systems (e.g., retractable lead systems for use with cryostats).

FIG. 1 provides a side sectional view of a retractable lead system 100 formed in accordance with various embodiments. As seen in FIG. 1, the retractable lead system 100 has a vacuum end 102 and an ambient end 104. The vacuum end 102 is oriented toward and disposed within a vacuum environment 103, and the ambient end 104 is orient toward and disposed within an ambient environment 105. The vacuum environment 103 is maintained at a lower pressure than the ambient environment 105. In various embodiments, the vacuum environment 103 is maintained at a relatively lower temperature than the ambient environment 105. For example, the vacuum environment 103 may be utilized in connection with a cryostat or supercooled system, such as a magnetic resonance imaging (MRI) system. As another example, the vacuum environment 103 may be associated with a turbine (e.g., a turbine used for energy or power generation). A boundary 109 separates the vacuum environment 103 from the ambient environment 105. Generally, the retractable lead system 100 is utilized in various embodiments to provide electrical signals (e.g., power) from the ambient environment 105 to inside the vacuum environment 103.

As seen in FIG. 1, the depicted retractable lead system 100 includes a cup 110, a seated contact 121, and a plunger 130. Generally, the plunger 130 is actuated between closed and open positions to electrically engage and disengage the seated contact 121, with the cup 110 providing support to the seated contact 121 and positioning the seated contact 121. With a portion of the plunger 130 in the ambient environment 105, and the seated contact 121 in the vacuum environment 103, the plunger 130 and seated contact 121 provide electrical communication between the ambient environment 105 and the vacuum environment 103 when engaged in the closed position (e.g., in physical contact with each other). To disrupt the electrical communication, the plunger 130 is actuated to the open position (the plunger 130 is shown in the open position in FIGS. 1 and 2). In the open position, the seated contact 121 and plunger 130 are separated by a gap 123 that is sufficiently large to prevent transmission to the seated contact 121 via the plunger 130.

Figure 2:
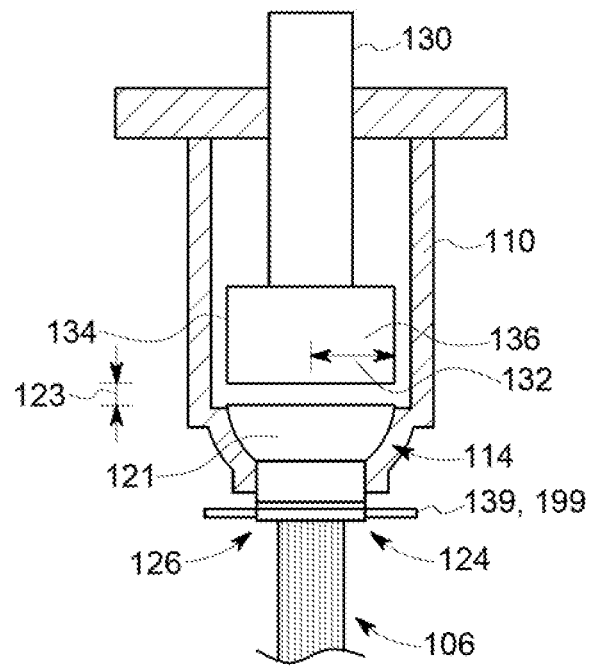
FIG. 2 provides a cross-sectional view of aspects of the retractable lead system of FIG. 1.
Figure 3:
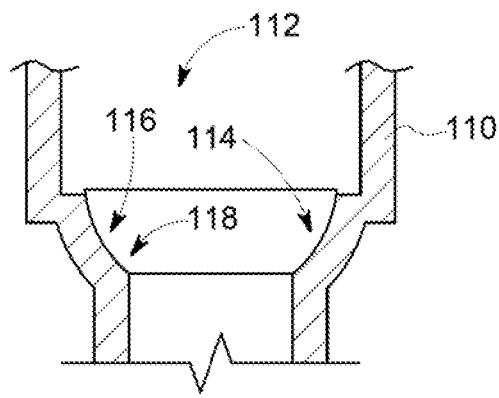
FIG. 3 provides a cross-sectional view of a cup of the retractable lead system of FIG. 1 in accordance with various embodiments.

As best seen in FIG. 1, the cup 110 is disposed proximate the vacuum end 102 of the retractable lead system 100. The cup 110 is disposed within the vacuum environment 103, and is generally configured to orient and support the seated contact 121. As seen in FIGS. 1-3, the cup 110 defines a cavity 112 and a contact reception seat 114. The cavity 112 is open ended (open on an end oriented toward the ambient end 104) and is configured to receive the seated contact 121, and the contact reception seat 114 defines a border of the cavity 112 proximate the vacuum end 102, with the contact reception seat 114 configured to contact, orient, and support the seated contact 121. In the illustrated example, the depicted contact reception seat 114 defines a spherical portion 116 that has a contact reception spherical radius 118. In various embodiments, the cup 110 is made of fiberglass (e.g. G10) or other electrically insulating material to inhibit any loss of current from the plunger 130 to the seated contact 121.

The seated contact 121 is disposed within the cup 110 and positioned proximate the vacuum end 102. As seen in FIGS. 1 and 2, the seated contact 121 is disposed within the contact reception seat 114. The seated contact 121 is configured to be electrically coupled to an interior lead 106 that is disposed within the vacuum environment 103. The seated contact 121 is made of electrically conductive material, and provides a pathway for current to flow to the interior lead 106 (and from the interior lead to one or more components within the vacuum environment 103) from the plunger 130 when the plunger 130 is in the closed position.

Figure 4:
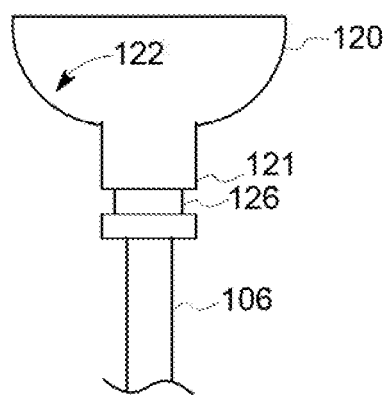
FIG. 4 provides a cross-sectional view of a seated contact of the retractable lead system of FIG. 1 in accordance with various embodiments.

In the example depicted in FIGS. 1, 2, and 4, the seated contact 121 is configured as a spherical contact 120 that is disposed within the contact reception seat 114 (e.g., proximate the spherical portion 116 of the contact reception seat 114). The depicted spherical contact 120 defines a contact spherical radius 122 that corresponds to the contact reception spherical radius 118 of the contact reception seat 114 of the cup 110. For example, the contact spherical radius 122 may be sized as closely as possible or practical within manufacturing capabilities to the contact reception spherical radius 118. Accordingly, a hemisphere defined by the spherical contact 120 may fit as closely as possible or practical adjacent to a hemisphere defined by the contact reception seat 114 of the cup 110. Generally, the closely matched hemispherical shapes of the spherical contact 120 and the contact reception seat 114 of the illustrated example help provide less resistance to movement and/or help avoid high point loads to help promote more uniform loading between the spherical contact 120 and the cup 110 relative to other shapes. It may be noted, however, that alternate contact and seat shapes, such as flat, conical, or other shapes may be used in alternate embodiments.

In the illustrated embodiment, as best seen in FIG. 2, the spherical contact 120 includes a distal end 124 that projects beyond the cup 110 (e.g., deeper into the vacuum environment 103). The depicted retractable lead system includes a retention member 139 coupled to the distal end 124 of the spherical contact 120. For example, the retention member 139 may include a snap ring 199 that fits in a groove 126. The retention member 139 helps maintain the spherical contact 120 at or near the contact reception seat 114 when the plunger 130 is in the open position.

As best seen in FIGS. 1 and 2, the depicted plunger 130 has an ambient contact 132 and a retractable contact 134. The plunger 130 is made of a conductive material (e.g., copper) to allow passage of current between the ambient contact 132 and retractable contact 134 (e.g., via a core 151 of the plunger 130). In the illustrated example, the ambient contact 132 and retractable contact 134 are disposed on opposite ends of the plunger 130, with the ambient contact 132 disposed on an ambient end 131 of the plunger 130, and the retractable contact 134 disposed on a vacuum end 133 of the plunger 130. In the illustrated embodiment, the ambient contact 132 is disposed in the ambient environment 105 and configured to receive an electrical signal from a source disposed within the ambient environment. For example, the depicted ambient end 131 is coupled to a clamp 135 through which a signal is delivered to the plunger 130 from the exterior lead (not shown). The illustrated retractable contact 134 is disposed within the vacuum environment 103 and configured to deliver an electrical signal to the seated contact 121 when the plunger 130 is in the closed position. The plunger 130 is configured to be actuated between an open position at which the retractable contact 134 is retraced from the spherical contact 120 and closed position at which the retractable contact 134 is coupled with the spherical contact 120. The plunger 130, for example, may be actuated manually by an operator. In the open position, a signal is inhibited from passing through the plunger 130 to the spherical contact 120. In the closed position, a signal is allowed to pass through the plunger 130 to the spherical contact 120.

As seen in FIGS. 1 and 2, the depicted example retractable contact 134 of the plunger 130 is configured as a cylindrical contact 136. The cylindrical contact 136 has a generally cylindrical shape (with the axis of the cylinder defined by the cylindrical contact 136 extending along an axis passing along the center of the plunger 130) having a radius 137 corresponding to the contact spherical radius 122 of the spherical contact 120. For example, the radius 137 may be as closely sized to the contact spherical radius 122 as possible or practical using conventional manufacturing techniques.

In various embodiments, a sealing member is provided to seal the vacuum environment 103 from the ambient environment 105 to help maintain the pressure differential therebetween. The sealing member may also provide a thermal barrier to help maintain a temperature difference between the ambient environment 105 and the vacuum environment. In the illustrated embodiment, a sealing member 140 is provided within the plunger 130, such that the sealing member 140 moves with the plunger 130, thereby avoiding any rubbing contact between the sealing member 140 and the plunger 130.

In the illustrated embodiment, as seen in FIG. 1, the retractable lead system 100 includes a vacuum end plate 141 along with the sealing member 140. The vacuum end plate 141 defines a portion of the boundary 109 between the vacuum environment 103 and the ambient environment 105. The plunger 130 moves relative to the vacuum end plate 141 when moved between the open and closed positions. As seen in FIG. 1, the vacuum end plate 141 has an opening 143 through which the plunger 130 passes. The sealing member 140 is disposed a distance D from the vacuum end plate 141.

In various embodiments, the plunger 130 includes a hollow portion in which the sealing member 140 is disposed. As seen in FIG. 1, in the illustrated embodiment, the plunger 130 includes a plunger sleeve 150 that is disposed radially about at least a portion of the plunger 130 (e.g., is configured as a cylindrical tube extending along a portion of the length of the plunger and about a core 151 of the plunger). The sealing member 140 in the illustrated embodiment is disposed within the plunger sleeve 150. For example, the sealing member 140 may be welded along its periphery to the inner surface of the plunger sleeve 150 as well as to the core 151 to help provide an effective seal. The sealing member 140, for example, may be made of electrically and thermally insulating ceramic, and be configured as an annular plug 142 inserted into the plunger sleeve 150, with the sealing member 140 interposed between the core 151 and plunger sleeve 150, and joined to each of the core 151 and plunger sleeve 150 to provide a sealing barrier (e.g., welded). In the illustrated embodiment, the plunger sleeve 150 and the core 151 extend from a plunger plate 155. The sealing member 140 may abut or contact the plunger plate 155.

In various embodiments, the plunger 130 may include a bellows or other resiliently biasable portion joined to and/or forming a portion of the plunger sleeve 150. Generally, the bellows allows from compression and/or expansion along its length to accommodate movement of the plunger 130 (e.g., movement of the retractable contact 134 into and out of contact with the seated contact 121. In the illustrated embodiment, the plunger 130 includes a bellows 152 coupled to the plunger sleeve 150. The bellows 152 is interposed between the vacuum end plate 141 and the sealing member 140 along the length of the plunger 140. The depicted bellows 152 extends from the plunger sleeve 150, and includes an end 153 that is joined (e.g., welded) to the vacuum end plate 141, with the end 153 radially surrounding the opening 143 through which the plunger 150 (e.g., the core 151 of the plunger 150) passes. The bellows 152 may be formed, for example, as a corrugated metal structure.

It may be noted that, with the sealing member 140 disposed away from the vacuum end plate 141, the boundary 109 between the vacuum environment 103 and the ambient environment 105 extends along the vacuum end plate 141, through the plunger sleeve 151 and along the length of the plunger sleeve 151 to the sealing member 140, and back along the length of the plunger sleeve 151 to the vacuum end plate 141. In various embodiments, using a sealing member 140 that is disposed a distance from the vacuum end plate 141 through which the plunger moves 130 and also moves along with the plunger 130 allows for improved sealing of the vacuum environment 103 from the ambient environment 105 (e.g., an improved seal relative to a stationary seal located proximate the vacuum end plate 141 and abutting the plunger 130 that does not move with the plunger 130). Further, joining the expanding and contracting bellows 152 at a stationary end 153 to the vacuum end plate 141 also avoids movement between joined sealed surfaces.

In various embodiments, a spring assembly is utilized to provide a load to the plunger 130 and help provide a desired contact pressure between the plunger 130 and the seated contact 121. As best seen in FIG. 1, the depicted retractable lead system 100 includes a drive stud 160 and drive nut 162. The drive stud 160 is coupled to the plunger 130. For example, in various embodiments, the drive stud 160 is coupled to the plunger 130 via a drive plate 190, as also discussed below. The depicted retractable lead assembly 100 also includes a resiliently biasable spring assembly 170 that is disposed radially about the drive stud 160. Generally, a torque on drive nut 162 provides a desired force loading, with the spring assembly 170 helping to maintain the load in a near static condition regardless of thermal and/or mechanical changes in the environment in which the retractable lead system 100 is disposed. The depicted drive stud 170 is fixed to an end plate 163 that is stationary, so that the position of the plunger 130 relative to end plate 163 may be set or maintained using the retention nut 164.

Figure 5:
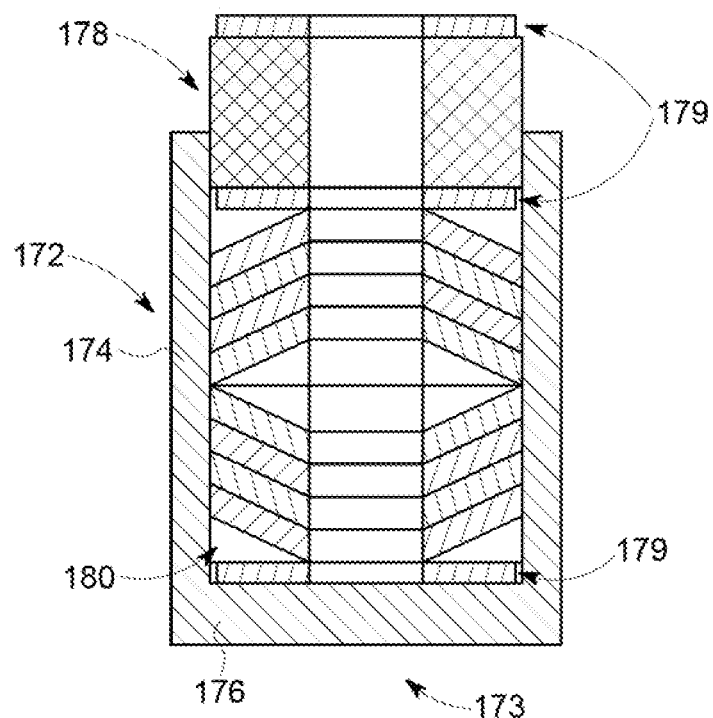
FIG. 5 provides a side sectional view of a spring cup and related components in accordance with various embodiments.

In some embodiments, a spring cup may be utilized to help position the spring assembly 170 and maintain the spring assembly 170 in a desired position. FIG. 5 provides a side sectional view of a spring cup 172 and related components. As seen in FIGS. 1 and 5, the depicted retractable lead system 100 includes a spring cup 172. The spring cup has sides 174 extending from a bottom 176 of the spring cup 172. The spring cup 172 is disposed radially about the drive stud 160, and includes an opening 173 sized to allow passage of the drive stud 160. One or more spring members 180 of the spring assembly 170 is interposed between the sides 174 of the spring cup 172 and the drive stud 160. Generally, the spring cup 172 helps prevent radial movement of the spring assembly 170, thereby preventing the spring assembly 170 (e.g., members 180) from interacting undesirably with the threads of the drive stud 160. It may be noted that the spring members 180 in various embodiments include a series of Belleville washers. The Belleville washers may arranged in a series extending along an axis defined by the drive stud 160, with the number, size, and orientations of the Belleville washers selected to provide a desired force to maintain the contact load within a predetermined range. The spring cup 172 in various embodiments is formed of a fiberglass (e.g., G10).

As also seen in FIGS. 1 and 5, the illustrated embodiment also includes a drive spacer 178 that is interposed between the drive stud 160 and spring members 180. The drive spacer 178 transfers force from the drive stud 160 to the spring members 180, and helps provide a more uniform force distribution on the spring members 180. Washers 179 are also utilized to help provide more uniform force distribution between various components depicted in FIGS. 1 and 5.

In some embodiments, more than one plunger may be actuated by a single drive stud. For example, as seen in FIG. 1, two plungers—namely plunger 130 and plunger 130A—are actuated by a single drive stud 160. It may be noted that plunger 130A may be generally similar to plunger 130 discussed above. The depicted retractable lead system 100 includes a drive plate 190 that is interposed between the spring cup 172 and a retention nut 164 to secure the drive plate relative to the spring assembly 170 and drive nut 160. The drive plate 190 is coupled to the two plungers 130, 130A. For example, each plunger may be secured to the drive plate 190 via a corresponding opening 191. Accordingly, multiple plungers may be secured to a drive nut via a drive plate, so that a single drive nut and spring assembly may be utilized to actuate multiple plungers.

Figure 6:
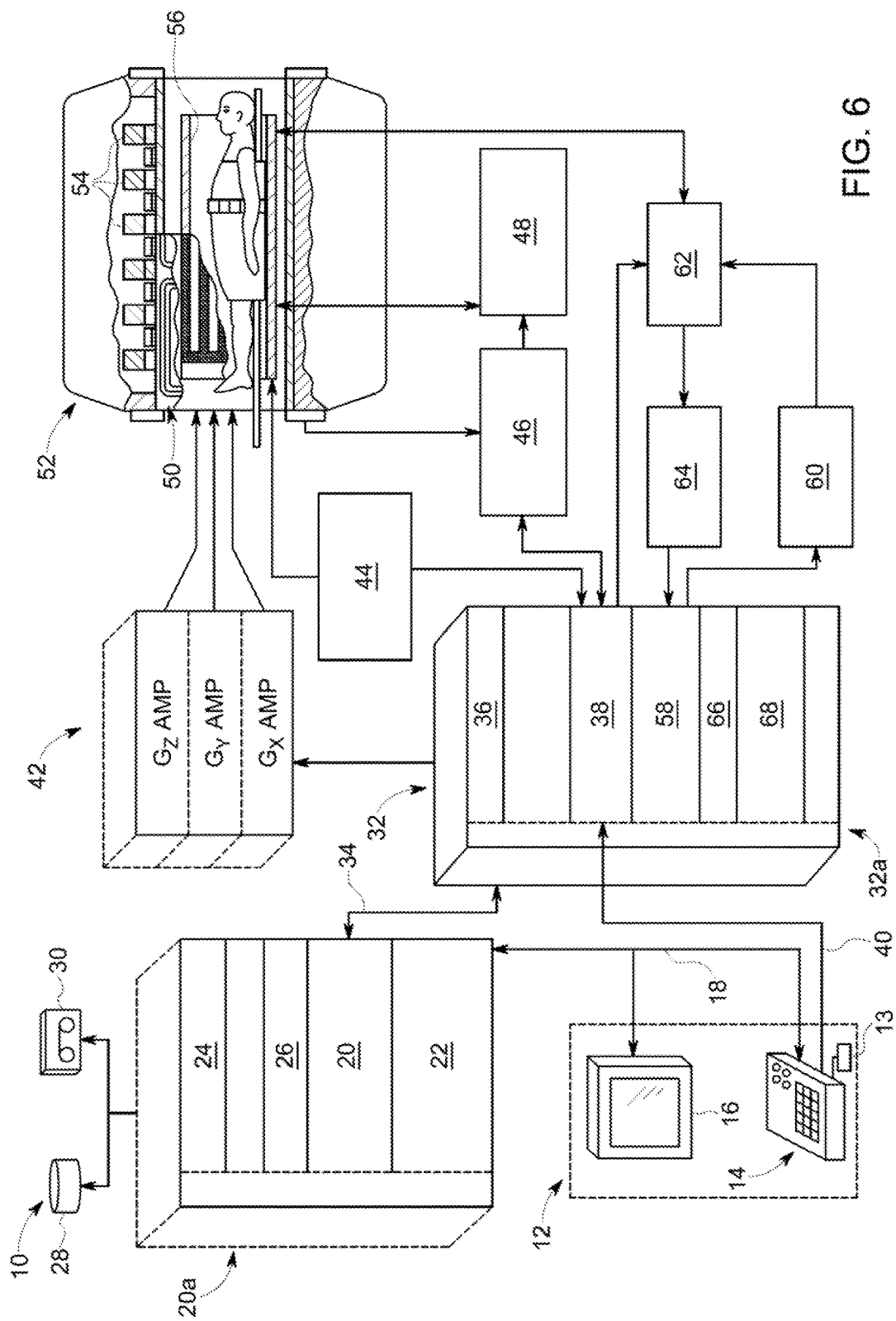
FIG. 6 provides a schematic view of a magnetic resonance imaging (MRI) system in accordance with various embodiments.

As discussed herein various methods and/or systems (and/or aspects thereof) described herein may be implemented in connection with an MRI system. For example, FIG. 6 depicts various major components of an MRI system 10 formed in accordance with various embodiments. The operation of the system is controlled from an operator console 12 which includes a keyboard or other input device 13, a control panel 14, and a display 16. The console 12 communicated through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and recordable media 30 for storage of image data and programs, and communicates with a separate system control 32 through a high speed serial link 34. The input device 13 can include a mouse, joystick, keyboard, track ball, touch activated screen, light want, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the san sequence that is to be performed. The pulse generator module 38 operates the system components to carry out the desired scan sequence and produce data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensor connected to the patient or subject, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 and RF shield (not shown) form a part of a magnet assembly 52 which includes a polarizing magnet 54 and a RF coil assembly 56. A transceiver module 58 in the system control 32 produces pulses which are amplified by an RF amplifier 60 and coupled to the RF coil assembly 56 by a transmit/receive switch 62. The resulting signals emitted by the excited nuclei in the patient may be sensed by the same RF coil assembly 56 or apportion thereof and coupled through transmit/receive switch 62 to a preamplifier 64. The amplified MR signals are demodulated, filtered, and digitized in the receive section of the transceiver 58. The transmit/receive switch 62 is controlled by a signal from the pulse generator module 38 to electrically connect the RF amplifier 60 to the coil assembly 56 during the transmit mode and to connect the preamplifier 64 to the coil assembly 56 during the receive mode. The transmit/receive switch 62 can also enable a separate RF coil (for example, a surface coil) to be used in either the transmit or receive mode. The magnet assembly 52 may be cooled cryogenically.

The MR signals picked up by the selected RF coil are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless or until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A retractable lead system comprising:
   a cup disposed proximate a vacuum end of the retractable lead system, the cup defining a cavity and a contact reception seat, the contact reception seat defining a spherical portion having a contact reception spherical radius;
   a spherical contact disposed within the contact reception seat, the spherical contact defining a contact spherical radius that corresponds to the contact reception spherical radius, the spherical contact configured to be electrically coupled to an interior lead disposed within a vacuum environment; and
   a plunger comprising an ambient contact and a retractable contact disposed on opposite ends of the plunger, the ambient contact disposed proximate an ambient end of the retractable lead system, the plunger configured to be actuated between an open position at which the retractable contact is retracted from the spherical contact and a closed position at which the retractable contact is coupled with the spherical contact.

2. The retractable lead system of claim 1, wherein the retractable contact comprises a cylindrical contact having a radius corresponding to the contact spherical radius of the spherical contact.

3. The retractable lead system of claim 1, wherein the spherical contact includes a distal end projecting beyond the cup, the retractable lead system comprising a retention member coupled to the distal end of the spherical contact.

4. The retractable lead system of claim 1, further comprising a sealing member configured to be disposed a distance from a vacuum end plate disposed proximate a boundary of the vacuum environment and having an opening through which the plunger passes, wherein the plunger moves relative to a vacuum end plate when moved between the open and closed positions.

5. The retractable lead system of claim 4, wherein the plunger comprises a plunger sleeve disposed radially about at least a portion of the plunger, the sealing member disposed within the plunger sleeve.

6. The retractable lead system of claim 5, further comprising a bellows coupled to the plunger sleeve and interposed between the vacuum end plate and the sealing member.

7. The retractable lead system of claim 5, wherein the sealing member comprises an annular plug formed of ceramic and disposed within and coupled to the plunger sleeve.

8. The retractable lead system of claim 1, further comprising a drive stud and drive nut, the drive stud coupled to the plunger, the system further comprising a resiliently biasable spring assembly disposed radially about the drive stud.

9. The retractable lead system of claim 8, wherein the spring assembly comprises a spring cup having sides extending from a bottom, the spring cup disposed radially about the drive stud, with one or more spring members interposed between the sides of the spring cup and the drive stud.

10. The retractable lead system of claim 9, further comprising a drive spacer interposed between the drive stud and spring members.

11. The retractable lead system of claim 10, wherein the system comprises at least two plungers, the system further comprising a drive plate interposed between the spring cup and a retention nut, the drive plate coupled to the at least two plungers.

12. A retractable lead system comprising:
    a cup disposed proximate a vacuum end of the retractable lead system, the cup defining a cavity and a contact reception seat;
    a seated contact disposed within the contact reception seat, the seated contact configured to be electrically coupled to an interior lead disposed within a vacuum environment;
    a plunger comprising an ambient contact and a retractable contact disposed on opposite ends of the plunger, the ambient contact disposed proximate an ambient end of the retractable lead system, the plunger configured to be actuated between an open position at which the retractable contact is retracted from the seated contact and a closed position at which the retractable contact is coupled with the seated contact; and a sealing member configured to be disposed a distance from a vacuum end plate disposed proximate a boundary of the vacuum environment and having an opening through which the plunger passes, the plunger moving relative to the vacuum end plate when moved between the open and closed positions.

13. The retractable lead system of claim 12, wherein the plunger comprises a plunger sleeve disposed radially about at least a portion of the plunger, the sealing member disposed within the plunger sleeve.

14. The retractable lead system of claim 13, further comprising a bellows coupled to the plunger sleeve and interposed between the vacuum end plate and the sealing member.

15. The retractable lead system of claim 13, wherein the sealing member comprises an annular plug formed of ceramic and disposed within and coupled to the plunger sleeve.

16. The retractable lead system of claim 12, further comprising a drive stud and drive nut, the drive stud coupled to the plunger, the system further comprising a resiliently biasable spring assembly disposed radially about the drive stud.

17. A retractable lead system comprising:
   a cup disposed proximate a vacuum end of the retractable lead system, the cup defining a cavity and a contact reception seat;
   a seated contact disposed within the contact reception seat, the seated contact configured to be electrically coupled to an interior lead disposed within a vacuum environment;
   a plunger comprising an ambient contact and a retractable contact disposed on opposite ends of the plunger, the ambient contact disposed proximate an ambient end of the retractable lead system, the plunger configured to be actuated between an open position at which the retractable contact is retracted from the seated contact and a closed position at which the retractable contact is coupled with the seated contact;
   a drive stud and drive nut, the drive stud coupled to the plunger, and
   a resiliently biasable spring assembly disposed radially about the drive stud.

18. The retractable lead system of claim 17, wherein the spring assembly comprises a spring cup having sides extending from a bottom, the spring cup disposed radially about the drive stud, with one or more spring members interposed between the sides of the spring cup and the drive stud.

19. The retractable lead system of claim 18, further comprising a drive spacer interposed between the drive stud and spring members.

20. The retractable lead system of claim 19, wherein the system comprises at least two plungers, the system further comprising a drive plate interposed between the spring cup and a retention nut, the drive plate coupled to the at least two plungers.

* * * * *